United States Patent
Simmerer et al.

[11] Patent Number: 6,099,750
[45] Date of Patent: Aug. 8, 2000

[54] USE OF ORGANIC COMPOUNDS IN THE PLASTIC COLUMNAR DISCOTIC LIQUID-CRYSTAL PHASE FOR TRANSPORT OF ELECTRIC CHARGES

[75] Inventors: Jürgen Simmerer, Erlangen; Karl-Heinz Etzbach; Karl Siemensmeyer, both of Frankenthal; Wolfgang Paulus, Weisenheim; Peter Schuhmacher, Mannheim; Birgit Glüsen, Ritterhude; Helmut Ringsdorf, Mainz; Joachim H. Wendorff, Marburg; Dietrich Haarer, Bayreuth; Andreas Kettner, Nienburg, all of Germany

[73] Assignee: Siemens Aktiengesellschaft, Munich, Germany

[21] Appl. No.: 09/077,167
[22] PCT Filed: Nov. 25, 1996
[86] PCT No.: PCT/DE96/02262
  § 371 Date: Nov. 20, 1998
  § 102(e) Date: Nov. 20, 1998
[87] PCT Pub. No.: WO97/19142
  PCT Pub. Date: May 29, 1997

[30] Foreign Application Priority Data

Nov. 23, 1995 [DE] Germany ............ 195 43 637

[51] Int. Cl.[7] ............ C09K 19/58; C09K 19/32; G03G 15/00
[52] U.S. Cl. ............ 252/299.3; 252/299.62; 430/56
[58] Field of Search ............ 252/299.62, 299.3; 430/56

[56] References Cited

U.S. PATENT DOCUMENTS

| | | | |
|---|---|---|---|
| 4,430,650 | 2/1984 | Billard et al. | 340/784 |
| 4,631,143 | 12/1986 | Praefcke et al. | 252/299.2 |
| 4,657,694 | 4/1987 | Heeger et al. | 252/299.01 |
| 4,769,448 | 9/1988 | Heegere et al. | 534/804 |
| 5,384,068 | 1/1995 | Bock et al. | 252/299.01 |
| 5,635,105 | 6/1997 | Kawata et al. | 252/299.01 |
| 5,718,838 | 2/1998 | Okazaki | 252/299.01 |
| 5,730,903 | 3/1998 | Okazaki | 252/299.62 |
| 5,736,068 | 4/1998 | Haeussling et al. | 252/299.62 |
| 5,750,050 | 5/1998 | Goodby et al. | 252/299.62 |

*Primary Examiner*—C. H. Kelly
*Attorney, Agent, or Firm*—Kenyon & Kenyon

[57] ABSTRACT

Use of compounds in the plastic columnar discotic liquid-crystal phase for transport of electric charges.

14 Claims, 5 Drawing Sheets

USE OF ORGANIC COMPOUNDS IN THE PLASTIC COLUMNAR DISCOTIC LIQUID-CRYSTAL PHASE FOR TRANSPORT OF ELECTRIC CHARGES

FIELD OF THE INVENTION

The present invention relates to the use of compounds which are in the plastic columnar discotic liquid-crystal phase for transport of electric charges.

In addition, the invention relates to electronic components containing these compounds and mixtures of these compounds with columnar discotic helical and/or columnar discotic liquid-crystal compounds.

BACKGROUND OF THE INVENTION

Photoconductive organic polymers are an interesting class of materials and are used on a large scale industrially in copiers, laser printers and offset printing plates. Discotic liquid-crystal compounds such as hexapentyloxytriphenylenes having charge carrier mobilities of approx. $10^{-3}$ $cm^2/Vs$ are of special interest as organic photoconductors (Adam et al., *Physical Review Letters* 70 (1993) 457–460).

Some discotic columnar liquid-crystal compounds are known to be able to form higher-order phases in addition to or instead of a columnar phase. For example, older German patent application P4429597.9 describes discotic columnar liquid-crystal compounds which form a higher-order helical phase in certain temperature ranges. Such liquid-crystal phases have a high charge carrier mobility. However, many of these known organic photoconductors leave much to be desired regarding their chemical stability.

SUMMARY OF THE INVENTION

The object of the present invention was therefore to provide organic compounds that have liquid-crystal properties and have a high photoconductivity and charge carrier mobility with good chemical stability in the liquid-crystal state, and are suitable for use as charge transport compounds in photocopiers or in electronic components.

It has accordingly been found that liquid-crystal compounds which are in the plastic columnar discotic phase have an especially high charge carrier mobility and good chemical stability and that therefore compounds which are in this liquid-crystal phase are especially suitable for transport of electric charges.

DETAILED DESCRIPTION OF THE INVENTION

Figure 1:
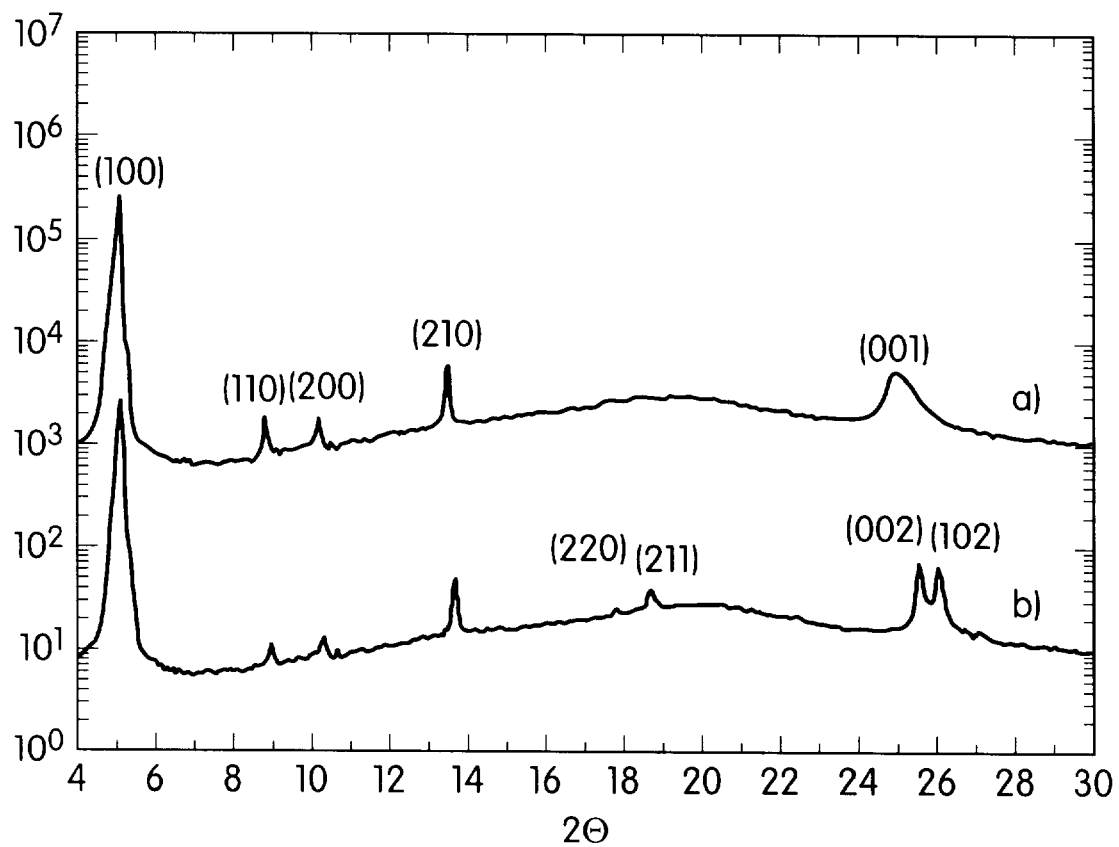

Plastic columnar discotic phase is understood here to refer to a liquid-crystal phase which is a state of order between the crystalline state and the discotic columnar liquid-crystal state. This state of order can be observed in heating from the crystalline state or in cooling from the isotropic liquid state or less ordered liquid-crystal state. Although the axes of the columns are oriented in the discotic columnar liquid-crystal state, the individual columns can move along their axes. This movement is so restricted in the plastic columnar discotic state that X-ray diffraction experiments yield mixed reflections (hkl) like those characteristic of the crystalline state. In contrast with the crystalline state, the plastic columnar discotic phases, however are mostly viscous and not solid, because the molecules can rotate about the axis of the column. Such liquid-crystal compounds can therefore be processed homogeneously over a large area and are also suitable for applications for which the dimension of crystalline semiconductors is a limiting factor. Especially with oligomeric compounds, the plastic columnar discotic phase can also be observed in the vitreous solidified state.

These plastic columnar discotic liquid-crystal phases usually have charge carrier mobilities of more than $10^{-2}$ $cm^2/Vs$. Any discotic liquid-crystal compounds having plastic columnar discotic phases in certain temperature ranges may be used according to this invention. Thus the compounds according to this invention may be derived from the following parent substances, for example: triphenylene, dibenzopyrene, benzene, naphthalene, anthracene, phenanthrene, benzophenanthrene, pentahelicene, perylene, decacyclene, truxene, rufigallol, pyrene, fluorene, indene, coronene or corresponding aromatic systems in which one or more ring carbons are replaced by nitrogen, oxygen or sulfur, or they may be derived from tricycloquinazoline, phthalocyanine or porphyrin.

With all these discotic liquid-crystal compounds, the substitution pattern must be selected so that the plastic columnar discotic liquid-crystal phase behavior occurs. This is especially frequently the case when the aromatic system is substituted by short aliphatic residues such as butyloxy, butylthio, pentyloxy or pentylthio. With many of these compounds, the symmetry of the compound is disturbed in such a manner that there is no axis of symmetry perpendicular to the plane of the molecule, but symmetrical compounds also exhibit the desired liquid-crystal phase behavior like hexabutyloxytriphenylene. The presence of the plastic columnar discotic liquid-crystal phase can be determined by simple polarization microscopic and differential calorimetric preliminary tests (occurrence of higher-order phases between columnar discotic and crystalline phase or between isotropic liquid and crystalline phase) and optionally confirmed by X-ray diffraction.

Preferred compounds for the uses according to this invention are substituted triphenylenes because the desired phase behavior is often observed with these compounds. Use of compounds having the structure of general formula I is especially preferred:

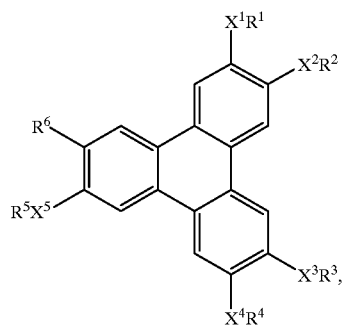

where the variables have the following meanings:

$X^1$, $X^2$, $X^3$, $X^4$, $X^5$ oxygen or sulfur $R^1$, $R^2$, $R^3$, $R^4$, $R^5$ butyl or pentyl and $R^6$ —CN, —O—$SO_2$—$CF_3$, —OCO—tert-butyl, —OCO—$CH_3$, —O—n—$C_4H_9$ or a substituent of the general formula:

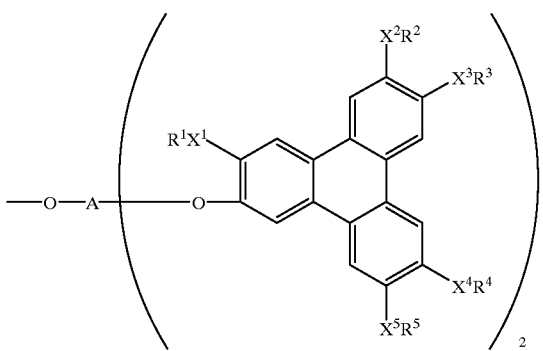

where A denotes

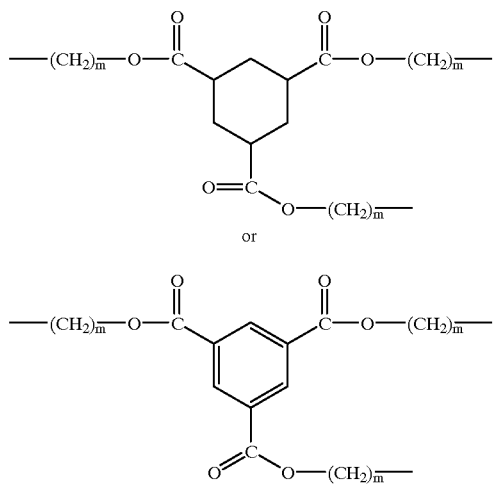

or
and m is an integer from 2 to 6.

Under these compounds, penta-n-pentyloxytriphenylenes having as additional substituent $R^6$ a cyano group, a triflate group, a pivaloyl group or an acetoxy group are especially preferred. Also especially preferred is 2,3,6,7,10,11-hexabutyloxytriphenylene because it has the desired liquid crystal behavior over a wide temperature range and also is especially easy to synthesize because of its symmetrical substitution.

In addition, compounds suitable for the uses according to this invention also include oligomeric or polymeric triphenylene derivatives, e.g., those that are trimerized via a central cyclohexanetricarboxylic acid group or benzenetricarboxylic acid group.

The desired liquid crystal phase behavior is also exhibited by triphenylene derivatives substituted with two or three hydroxypropyl groups, such as 2,6-dihydroxypropyl-3,7,10,11-tetrapentyloxytriphenylene, the corresponding 3,6-isomer and 3,6,10-trihydroxypropyl-2,7,11-tripentyloxytriphenylene.

The compounds according to this invention are used as photoconductors, for example, because of their high charge carrier mobility and their low conductivity in the dark. By photoionization, easy-to-transport free charge carriers can be produced in the compounds. These properties can be used, for example, in photovoltaic solar cells in which the compounds according to this invention can be used. In addition, the liquid crystal compounds according to this invention can be used in electronic components such as transistors, diodes or light-emitting diodes (LEDs).

Compounds that are suitable for use in light-emitting diodes, for example, will fluoresce in the visible range. In addition, it is possible to dope the liquid crystal phases according to this invention with fluorescent dyes and thus produce light emitting diodes.

In electronic components in which an increased conductivity in the dark is also desired in addition to photoconductivity, the liquid crystal phases according to this invention can also be mixed with dopants which increase conductivity in the dark. Such suitable dopants include, for example, $FeCl_3$, $AlCl_3$, chloranil, TNF (2,4,7-trinitrofluorenone) or TCNQ (2,3,5,6-tetracyanobenzoquinone).

The liquid crystal state of order on which the use according to this invention is based is manifested not only by pure compounds but also by mixtures of different plastic discotic columnar liquid crystal compounds and mixtures of these compounds with helical columnar discotic or discotic liquid crystal compounds. As a rule, it is desirable to obtain the desired liquid crystal behavior in the room temperature range in the broadest possible temperature interval, e.g., between 0 and 80° C. With pure liquid crystal compounds, however, this is often not the case. The phase temperatures and the phase widths can be varied through the synthesis of the aforementioned mixtures so that it is possible to obtain the desired liquid crystal behavior in different temperature ranges.

The synthesis of the compounds used according to this invention is known. For example, triphenylene derivatives can be synthesized according to the method described in the older German patent application 19517208.6 or the method described by Closs et al. in J. Chem. Soc. Perkin. Trans. I, 829 (1995). Synthesis of the oligomeric triphenylene derivatives is known from the older German patent application P 44 22 332.2.

EXAMPLES

Characterization Methods

Phase transition temperatures were determined by differential scanning calorimetry at a heating rate of 10 K/min.

The phase structures were determined by wide-angle X-ray scattering (WAXS) on a Siemens D-5000 diffractometer with a nickel filter and Cu-$K_\alpha$ radiation.

Phase Designations k crystalline $D_{ho}$ discotic columnar phase (hexagonal)

$D_{hp}$ plastic columnar discotic phase (hexagonal)

g vitreous, i.e. glassy i isotropic

EXAMPLE 1

3,6,7,10,11-Pentapentyloxytriphenylen-2-yl Pivaloate 181 mg (1.5 mmol) pivaloyl chloride was added to a solution of 673 mg (1 mmol) 2-hydroxy-3,6,7,10,11-pentapentyloxytriphenylene (see Henderson et al., *Liquid Crystals* 18 (1995) 191) in 1 mL pyridine. The mixture was heated for one hour at 80° C., diluted with diethyl ether and extracted repeatedly with dilute HCl and sodium carbonate solution. Purification was performed by crystallization from ethanol.

Yield: 72%

$^1$H-NMR (CDCl$_3$)

δ=8.00–7.76 ppm (m, 6 H, Ar-H), 4.30–4.18 ppm (m, 10 H, Ar-CH$_2$), 2.00–1.82 ppm (m, 10 H, ArCH$_2$C$\underline{H}_2$),
1.60–1.40 ppm (m, 20 H, Ar-CH$_2$CH$_2$(C$\underline{H}_2$)$_2$),
1.46 ppm (s, 9 H, C(C$\underline{H}_3$)$_3$,
1.02–0.92 (m, 15 H, Ar(CH$_2$)$_4$C$\underline{H}_3$);
$^{13}$C NMR (75 MHz, CDCl$_3$)

δ=172.0 ($\underline{C}$=O), 149.5, 149.4, 149.1, 148.6, 139.8 (O—substituted carbons of triphenylene)

127.7, 124.5, 123.6, 123.1, 123.0, 120.8 (internal carbons of triphenylene)

116.5, 108.1, 107.2, 106.9, 106.8, 105.5 (H-substituted carbons of triphenylene), 69.8, 69.7, 68.5, (Ar-$\underline{C}$H$_2$), 39.0 ($\underline{C}$(CH$_3$)$_3$), 29.0 (Ar-CH$_2$ $\underline{C}$H$_2$), 28.2 (Ar-CH$_2$CH2$\underline{C}$H$_2$), 27.3 (C($\underline{C}$H$_3$)$_3$), 22.4 (Ar-(CH$_2$).4$\underline{C}$H$_3$).

Phase Transition Behavior g-43° C. ? –5° C. D$_{hp}$ 65° C. D$_{ho}$ 178° C. i

Results of X-ray Diffraction

Table 1 shows the lattice constants a$_{hex}$, (h,k,l) indices and d distances for the X-ray reflections in the D$_{ho}$ phase (88° C.) and in the D$_{hp}$ phase (21° C.) in Å. The corresponding diffractogram is shown in FIG. 1 (a=D$_{ho}$ phase, b=D$_{hp}$ phase). The intensity of the X-ray reflection is plotted in arbitrary units as a function of the diffraction angle.

TABLE 1

| T[° C.] | a$_{hex}$ | (100) | (110) | (200) | (210) | (220) | (211) | (001) (002) | (102) |
|---|---|---|---|---|---|---|---|---|---|
| 88 | 20.04 | 17.36 | 10.03 | 8.73 | 6.57 | | | 3.55 | |
| 21 | 19.73 | 17.09 | 9.90 | 8.65 | 6.52 | 4.98 | 4.74 | 3.47 | 3.41 |

EXAMPLE 2

2,3,6,7,10,11-hexabutyloxytriphenylene

Phase Transition Behavior k 94° C. D$_{hp}$ 156° C. i

X-ray Diffraction

Figure 2:
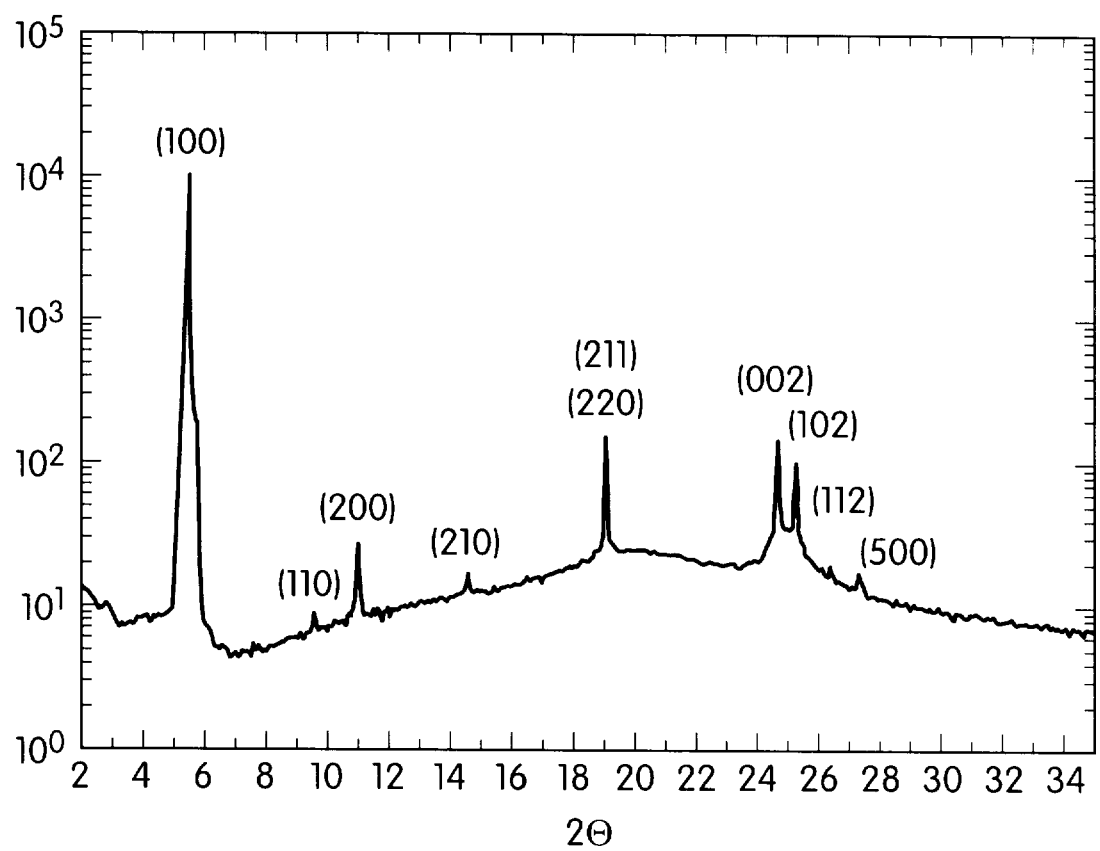

FIG. 2 shows the X-ray diffractogram of 2,3,6,7,10,11-hexabutyloxytriphenylene at 115° C.

Charge Carrier Mobility

The charge carrier mobility/photoconductivity was determined by time-of-flight measurement. To do so, charges were generated with the help of a laser pulse in the respective photoconductor layers with a basic voltage applied, and the time until the occurrence of the current signal was measured. Details of this method are described, for example, by D. Adam et al. in *Nature* 371 (1994) 141–143.

Figure 4:
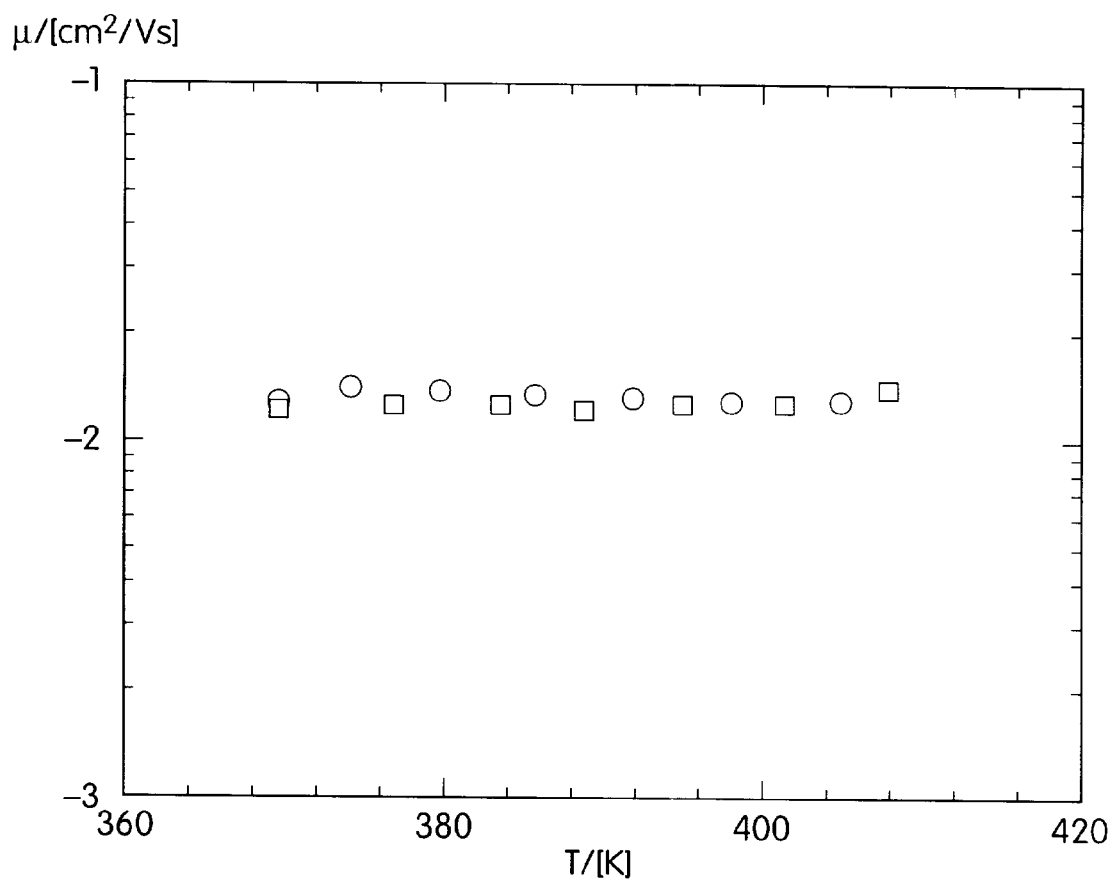

FIG. 4 shows the charge carrier mobility μ at different temperatures. The open circles show the variation of carrier mobility with cooling, and the filled squares indicate the variation of carrier mobility with heating.

Photoconductivity

Figure 5:
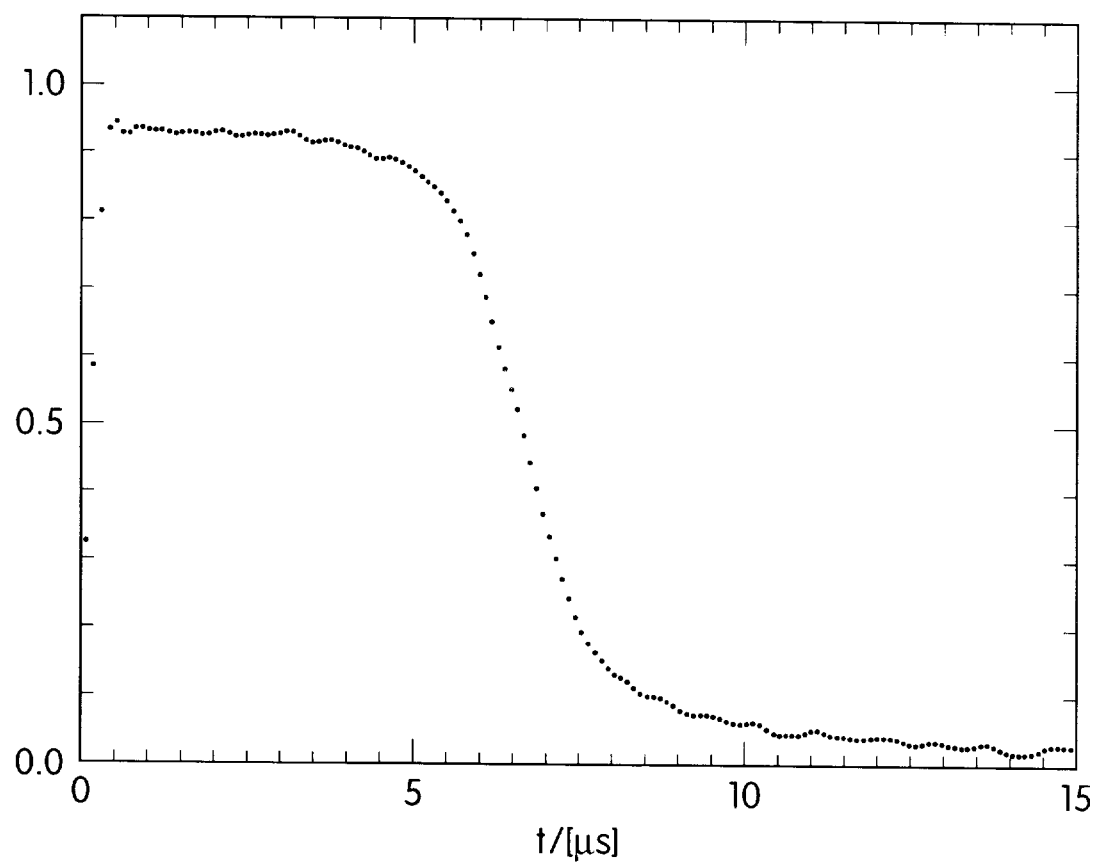

FIG. 5 shows the time dependence of a photocurrent after pulsed irradiation. The photocurrent is plotted in arbitrary units as a function of time.

EXAMPLE 3

3,6,7,10,11-pentapentyloxytriphenylen-2-yl triflate

Phase Transition Behavior k 54° C. D$_{hp}$ 84° C. D$_{ho}$ 182° C. i (Crystallization is possible only from solution; no crystallization and no glass transition were observed in cooling the pure substance down to –100° C.)

X-ray Diffraction

Figure 3:
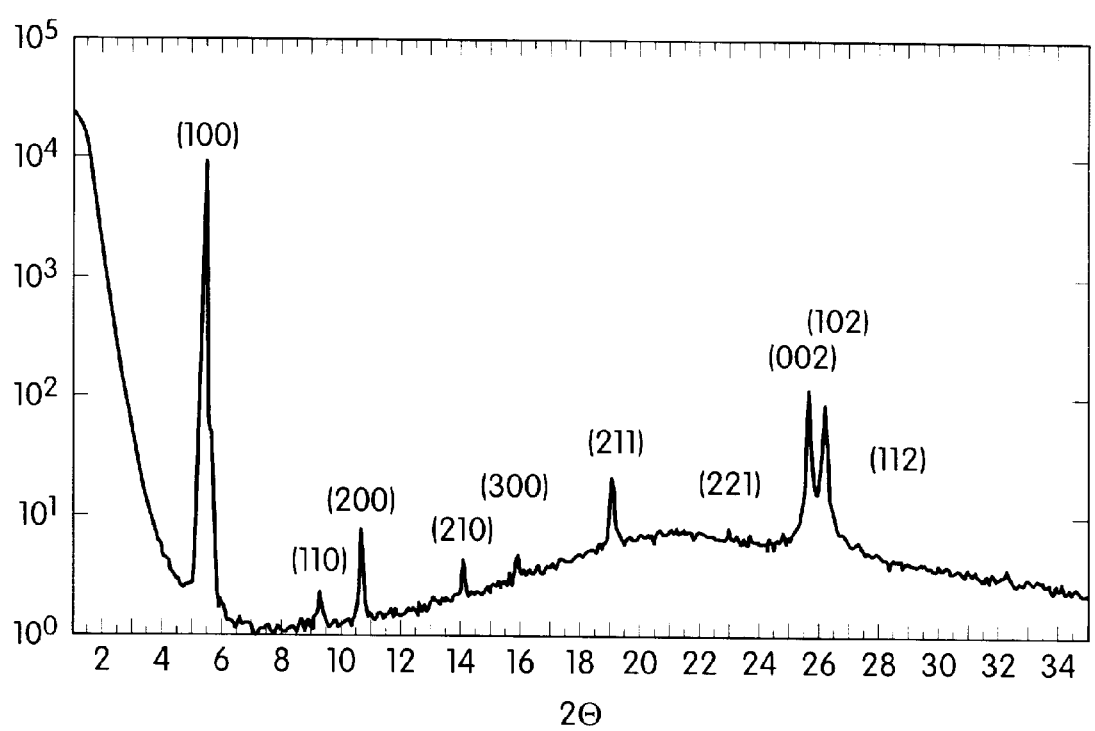

FIG. 3 shows the X-ray diffractogram of the compound at 110° C.

EXAMPLE 4

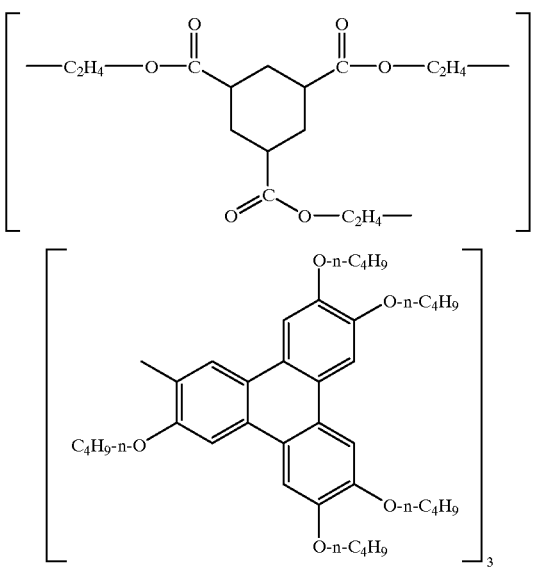

This compound can be synthesized by the methods described in the older German patent application P4422332.2 (the terminal bond lines denote the free valences for joining the two different parts of the molecule).

Phase Transition Behavior k<room temperature D$_{hp}$ 124° C. i

EXAMPLE 5

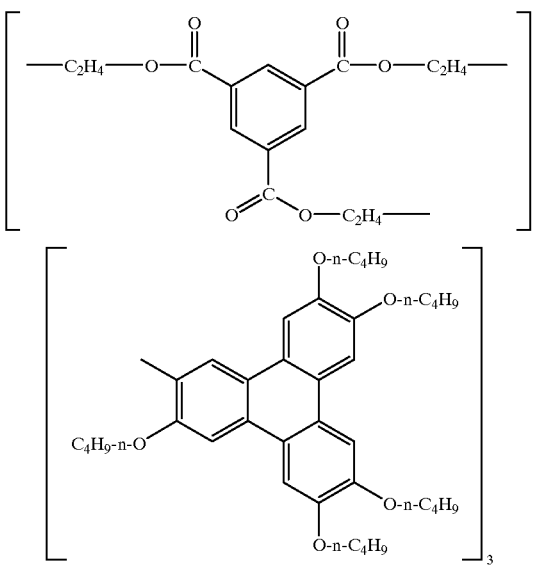

This compound can be synthesized by the methods described in older German patent application P4422332.2.

Phase Transition Behavior k 105° C. D$_{hp}$ 155° C. i

What is claimed is:

1. A process for transporting electric charges, which comprises:

a) providing an orpanic charge transporting compound, wherein the organic charge transporting compound is in the plastic columnar discotic liquid crystal phase;

b) producing electric charges in the organic charge transporting compound; and c) applying a voltage to the organic charge transporting compound.

2. The process of claim 1, wherein the compound is substituted triphenylene having the following structure:

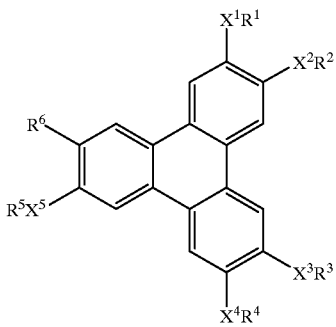

where:

$X^1, X^2, X^3, X^4, X^5$ oxygen or sulfur $R^1, R^2, R^3, R^4, R^5$ butyl or pentyl, and $R^6$ —CN, —O—SO$_2$—CF$_3$, —OCO-tert-butyl, —OCO—CH$_3$, —O—n—C$_4$H$_9$ or a substituent of the general formula:

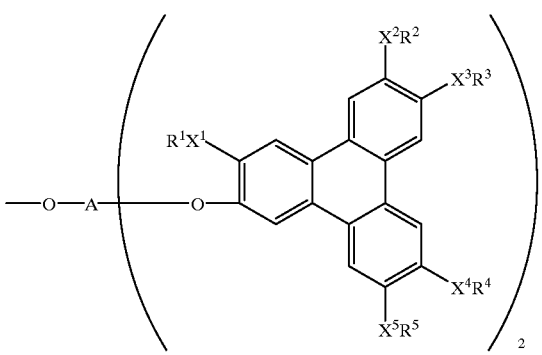

where A denotes

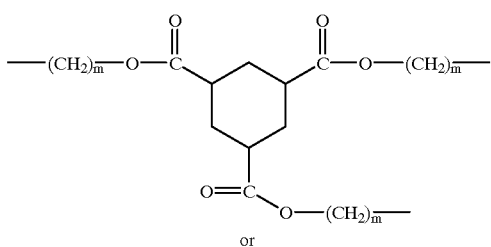

or

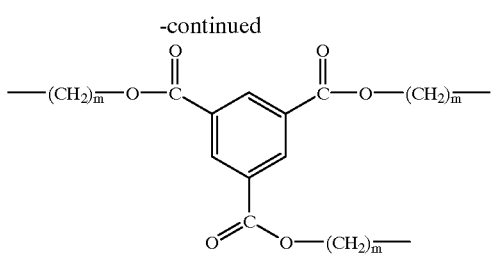

and m is an integer from 2 to 6.

3. The process of claim 2, wherein $X^1, X^2, X^3, X^4, X^5$ denote oxygen, $R^1, R^2, R^3, R^4, R^5$ denote n-pentyl and $R^6$ denotes —CN, —O—SO$_2$—CF, or —OCO-tert-butyl.

4. The process of claim 1, wherein the compound is 2, 3, 6, 7, 10, 11-hexabutyloxytriphenylene.

5. A photoconductor comprising a compound which is in the plastic columnar discotic liquid crystal phase.

6. The photoconductor of claim 5, wherein the compound is a substituted triphenylene having the following structure:

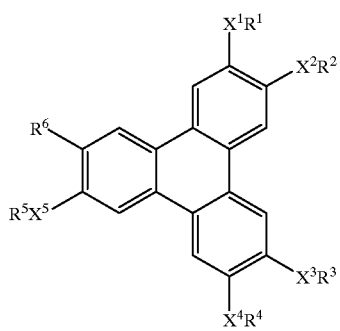

where:

$X^1, X^2, X^3, X^4, X^5$ oxygen or sulfur $R^1, R^2, R^3, R^4, R^5$ butyl or pentyl, and $R^6$ —CN, —O—SO$_2$—CF$_3$, —OCO-tert-butyl. —OCO—CH$_3$, —O—n—C$_4$H$_9$ or a substituent of the general formula:

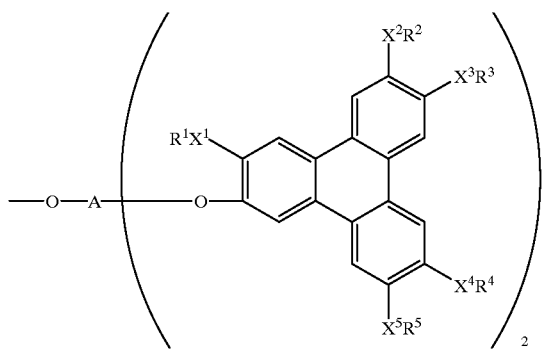

where A denotes

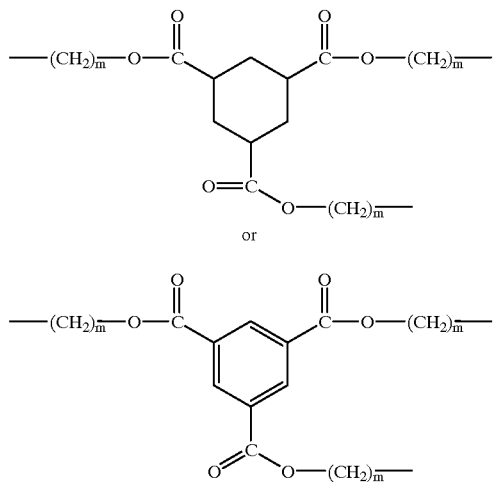

or

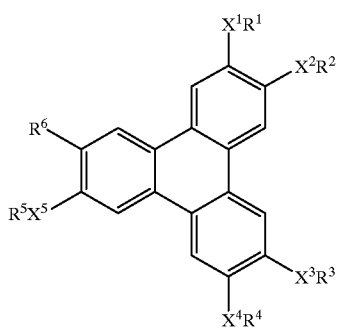

and m is an integer from 2 to 6.

7. An electronic component comprising a compound which is in the plastic columnar discotic liquid crystal phase.

8. The electronic component of claim 7, wherein the compound is a substituted triphenylene having the following structure:

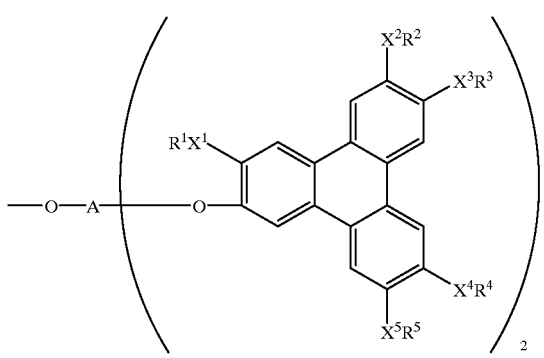

where:
$X^1$, $X^2$, $X^3$, $X^4$, $x^5$ oxygen or sulfur
$R^1$, $R^2$, $R^3$, $R^4$, $R^5$ butyl or pentyl, and
$R^6$ —CN, —O—SO$_2$—CF$_3$, —OCO-tert-butyl, —OCO—CH$_3$, —O—n—C$_4$H$_9$
or a substituent of the general formula:

where A denotes

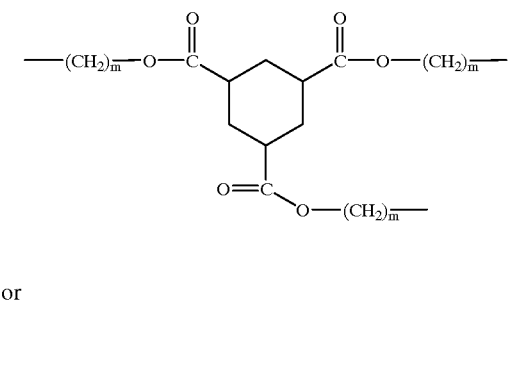

or

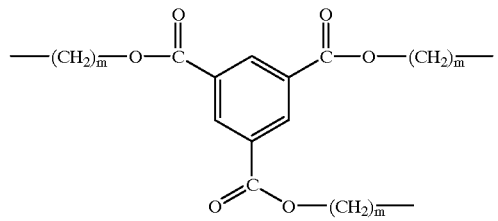

and m is an integer from 2 to 6.

9. A photovoltaic cell comprising a compound which is in the plastic columnar discotic liquid crystal phase.

10. The photovoltaic cell of claim 9, wherein the compound is a substituted triphenylene having the following structure:

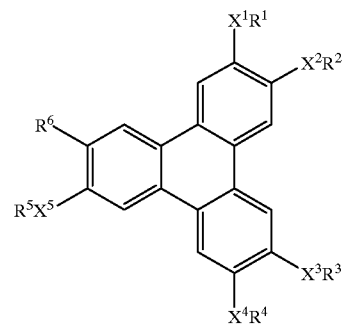

where:
$X^1$, $X^2$, $X^3$, $X^4$, $X^5$ oxygen or sulfur
$R^1$, $R^2$, $R^3$, $R^4$, $R^5$ butyl or pentyl, and
$R^6$ —CN, —O—SO$_2$—CF$_3$, —OCO-tert-butyl, —OCO—CH$_3$, —O—n—C$_4$H$_9$ or a substituent of the general formula:

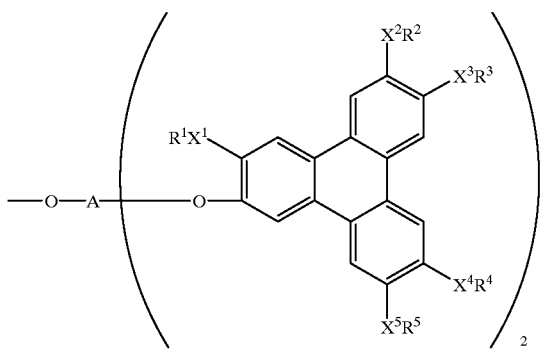

where A denotes

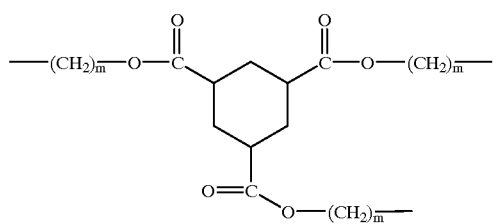

or

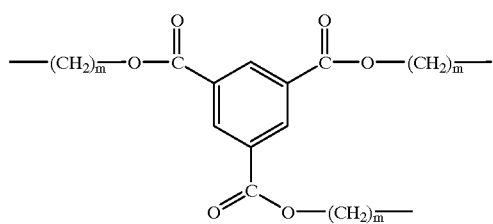

and m is an integer from 2 to 6.

11. A composition comprising a compound which is in the plastic columnar discotic liquid crystal phase and a columnar discotic helical compound.

12. The composition of claim 11, wherein the compound which is in the plastic columnar discotic liquid crystal phase is a substituted triphenylene having the following structure:

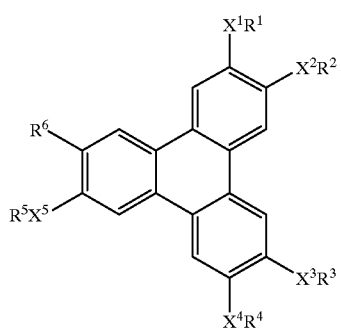

where:
$X^1$, $X^2$, $X^3$, $X^4$, $X^5$ oxygen or sulfur
$R^1$, $R^2$, $R^3$, $R^4$, $R^5$ butyl or pentyl, and
$R^6$ —CN, —O—$SO_2$—$CF_3$, —OCO-tert-butyl, —OCO—$CH_3$, —O—n—$C_4H_9$
or a substituent of the general formula:

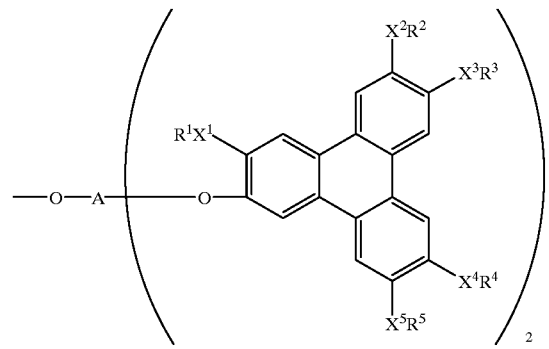

where A denotes

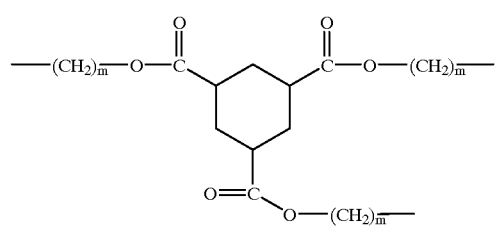

or

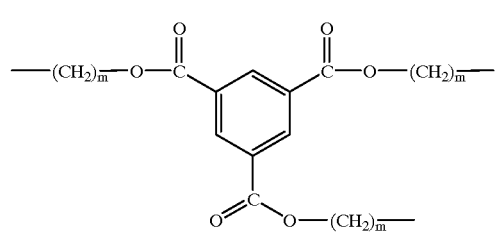

and m is an integer from 2 to 6.

13. A composition comprising a compound which is in the plastic columnar discotic liquid crystal phase and a columnar discotic liquid crystal compound.

14. The composition of claim 13, wherein the compound which is in the plastic columnar discotic liquid crystal phase is a substituted triphenylene having the following structure:

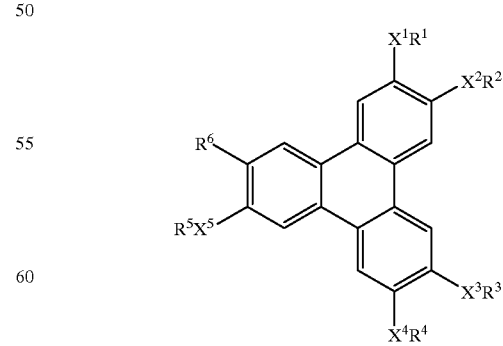

where:
$X^1$, $X^2$, $X^3$, $X^4$, $X^5$ oxygen or sulfur
$R^1$, $R^2$, $R^3$, $R^4$, $R^5$ butyl or pentyl, and $R^6$ —CN, —O—SO$_2$—CF$_3$, —OCO-tert-butyl, —OCO—CH$_3$, —O—n—C$_4$H$_9$
or a substituent of the general formula:
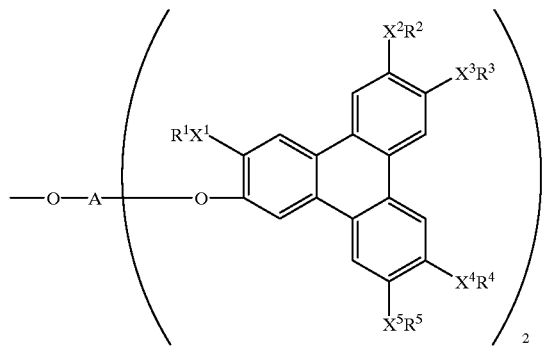
where A denotes
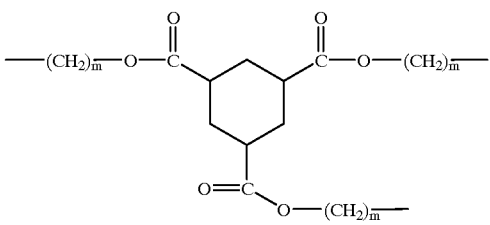
or
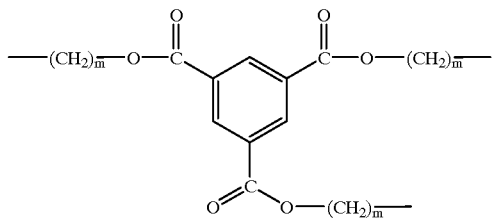
and m is an integer from 2 to 6.
* * * * *